US011963770B1

(12) United States Patent
Kahn et al.

(10) Patent No.: US 11,963,770 B1
(45) Date of Patent: Apr. 23, 2024

(54) CONNECTED AI-POWERED MEDITATION SYSTEM

(71) Applicants: Philippe R. Kahn, Santa Cruz, CA (US); Sonia Lee Kahn, Santa Cruz, CA (US); Arthur Kinsolving, Santa Cruz, CA (US); Mark Andrew Christensen, Santa Cruz, CA (US)

(72) Inventors: Philippe R. Kahn, Santa Cruz, CA (US); Sonia Lee Kahn, Santa Cruz, CA (US); Arthur Kinsolving, Santa Cruz, CA (US); Mark Andrew Christensen, Santa Cruz, CA (US)

(73) Assignee: DP Technologies, Inc., Scotts Valley, CA (US)

(*) Notice: Subject to any disclaimer, the term of this patent is extended or adjusted under 35 U.S.C. 154(b) by 632 days.

(21) Appl. No.: 16/746,782

(22) Filed: Jan. 17, 2020

Related U.S. Application Data

(60) Provisional application No. 62/793,886, filed on Jan. 17, 2019.

(51) Int. Cl.
| | |
|---|---|
| *A61B 5/16* | (2006.01) |
| *A61B 5/00* | (2006.01) |
| *A47C 15/00* | (2006.01) |
| *A61B 5/0205* | (2006.01) |
| *G09B 19/00* | (2006.01) |

(52) U.S. Cl.
CPC ............... *A61B 5/165* (2013.01); *A61B 5/16* (2013.01); *A61B 5/486* (2013.01); *A61B 5/7435* (2013.01); *A47C 15/004* (2013.01); *A61B 5/02055* (2013.01); *A61B 5/4854* (2013.01); *A61B 5/6891* (2013.01); *A61B 5/6892* (2013.01); *G09B 19/003* (2013.01)

(58) Field of Classification Search
CPC ......... A61B 5/00; A61B 5/0004; A61B 5/024; A61B 5/02405; A61B 5/0488; A61B 5/16; A61B 5/165; A61B 5/375; G06F 3/01; G06F 3/0346
See application file for complete search history.

(56) References Cited

U.S. PATENT DOCUMENTS

| | | | | |
|---|---|---|---|---|
| 5,676,138 A | * | 10/1997 | Zawilinski | A61B 5/389 600/301 |
| 9,802,129 B2 | * | 10/2017 | Murdock | A61B 5/0205 |
| 10,942,568 B2 | * | 3/2021 | Aimone | A61B 5/6803 |
| 2017/0215745 A1 | * | 8/2017 | Felix | A61B 5/7465 |
| 2017/0251967 A1 | * | 9/2017 | Premsukh | A61B 5/02405 |
| 2018/0364810 A1 | * | 12/2018 | Parshionikar | G06F 3/013 |
| 2019/0142349 A1 | * | 5/2019 | Schorey | A61B 5/11 600/546 |
| 2021/0265055 A1 | * | 8/2021 | Murdock | G16H 50/20 |

OTHER PUBLICATIONS

NPL Search (Apr. 26, 2022).*

* cited by examiner

*Primary Examiner* — Van T Trieu
(74) *Attorney, Agent, or Firm* — Nicholson De Vos Webster & Elliott LLP; Judith Szepesi

(57) ABSTRACT

A meditation system comprising a meditation surface including a contactless bio-sensor and a processor to analyze data from the contactless bio-sensor, to determine meditation results including a user's respiration, heart rate, and meditation quality, the processor further to calculate a recommendation to the user based on the meditation results. The system further comprising a user interface to display the meditation results and the recommendation.

22 Claims, 12 Drawing Sheets

Meditation Chair with contactless bio-sensing technology 330

Standard Chair Retrofitted with Meditation Surface including contactless bio-sensing technology 335

CONNECTED AI-POWERED MEDITATION SYSTEM

RELATED APPLICATION

The present application claims priority to U.S. Provisional Application No. 62/793,886, filed on Jan. 17, 2019, and incorporates that application in its entirety.

FIELD

The present application relates to meditation, and more particularly to a connected meditation system that provides feedback.

BACKGROUND

Meditation has been known to improve health as well as the ability to focus. Meditation is often a solitary activity, but sometimes done in a group setting, usually with a leader. The stilling of the mind, which is the focus of meditation, has been found to have health benefits.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A connected AI-powered meditation surface to provide improved meditation results is disclosed. The meditation surface may be a meditation mat, pillow, or chair, or other surface which includes a contactless bio-sensing technology. The meditation surface can monitor breathing, heart rate, depth of meditation. Using this data, the system can use AI-learning and cognitive behavioral science knowledge to score the meditation, as well as suggest improvements and options for a subsequent session. In one embodiment, the system can also integrate data from a sleep monitoring system, such as the system disclosed in co-pending application U.S. patent application Ser. No. 15/071,189, issued as U.S. Pat. No. 11,883,188, which is incorporated herein by reference. The meditation and sleep score can work together. The system can recommend meditation session(s) to make up for a sleep deficit, or sessions to improve sleep patterns.

Figure 1:
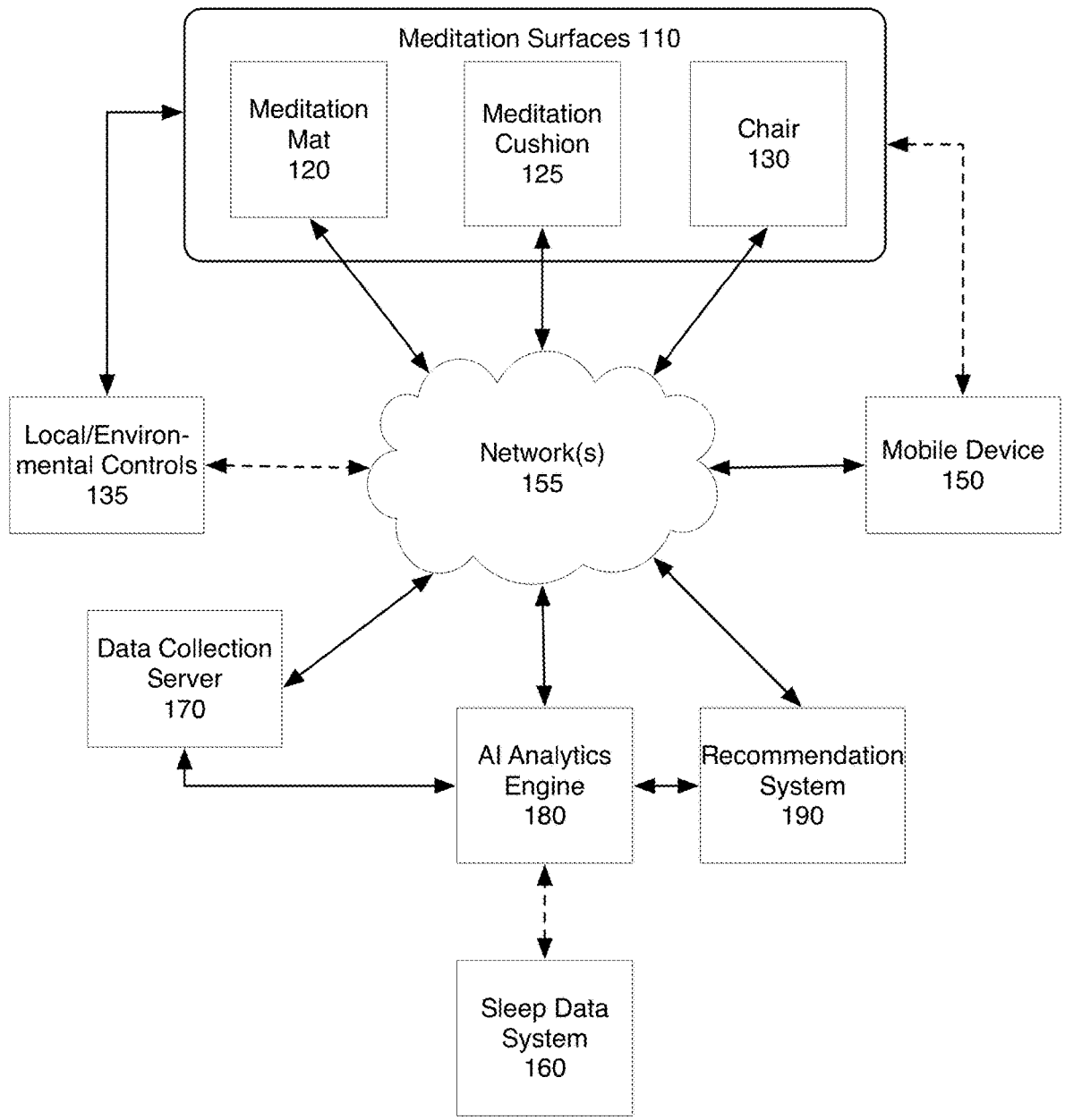
FIG. 1 is a system diagram showing one embodiment of the elements of the system.

FIG. 1 is a system diagram showing one embodiment of the elements of the system. The system includes a meditation surface 110 which may be a mat 120, cushion 125, chair 130, or other surface including one or more sensors. The meditation surface is designed to enable meditation by persons of any skill level and health. While for some people using a mat is not possible due to health issues, a mat, cushion, chair or other sensor-enabled meditation surface 110 is designed to accommodate everyone.

In one embodiment, the meditation surface 110 is coupled to a local/environmental control 135. Local environmental controls 135 in one embodiment monitor the local conditions (e.g. light level, temperature, humidity, sound scape, etc.) In one embodiment, local environmental controls 135 may permit adjusting of one or more of the local conditions. In one embodiment, the local environmental control 135 data is passed on to a data collection server 170. In one embodiment, the meditation surfaces 110 include sensors to detect the local environmental conditions. In one embodiment, in light of these local environmental conditions, the meditation surfaces 110 (and or mobile device/computer 150) may provide control signals to the local/environmental controls 135 to adjust conditions. For example, meditation may not be easy in a room with irregular noises. Turning on a white noise machine may improve the user's meditation. The system may automatically adjust such conditions when possible.

The meditation surface 110 is coupled to the network 155. In one embodiment, the meditation surface 110 itself includes wireless or cellular connectivity capability. In another embodiment, the meditation surface 110 may couple to a mobile device 150 or another base station, which in turns connects the meditation surface 110 to the network 155. In one embodiment, the mobile device 150 may also be used to provide feedback to the user utilizing the user interface of the mobile device 150. Of course, the mobile device 150 may be any computing device that can connect to a network, and display data to the user, including a laptop, desktop, tablet, etc.

Data collection server 170 collects the user data from the meditation surface(s) 110 and local environmental data from the meditation surface 110, local environmental controls 135 and/or mobile device 150. In one embodiment, there may be a number of data collection servers available. Inn one embodiment, all data flows to a data collection server. In one embodiment, data collection server 170 may be a cloud-based system rather than a computer.

The data is sent to an AI analytics engine 180. The AI analytics engine 180 analyzes the data and provides feedback to the user. In one embodiment, the feedback may be rapid, appearing in nearly real-time during the meditation session. In one embodiment, a low-interruption feedback mechanism may be used, like colors to indicate the depth of meditation, which does not interrupt the user but provides actionable near-real-time feedback. In one embodiment, the analytics are provided at the conclusion of the meditation session so as not to interrupt the meditation itself. In one embodiment, the AI analytics engine utilizes the user data and the local environmental data. In one embodiment, the AI-analytics engine 180 provides comparison data (how well the user is doing compared to others similarly situated).

In one embodiment, the AI analytics engine 180 may also receive data from other systems. For example, the AI analytics engine may receive data from a sleep data system 160. The sleep data system 160 receives user and environmental data from the user's sleep surface. For example, the sleep surface system described in co-pending U.S. patent application Ser. No. 15/071,189, issued as U.S. Pat. No. 11,883,188, may be used. In one embodiment, the AI analytics engine 180 may also receive data from other systems such as activity monitoring systems.

In one embodiment, the AI analytics engine 180 also interacts with a recommendation system 190 which provides recommendations for behavioral changes to the user. In one embodiment, behavioral changes may include meditation at a different time, altering sleep habits or eating habits, etc. The process of identifying recommendations is described in more detail below.

Figure 2:
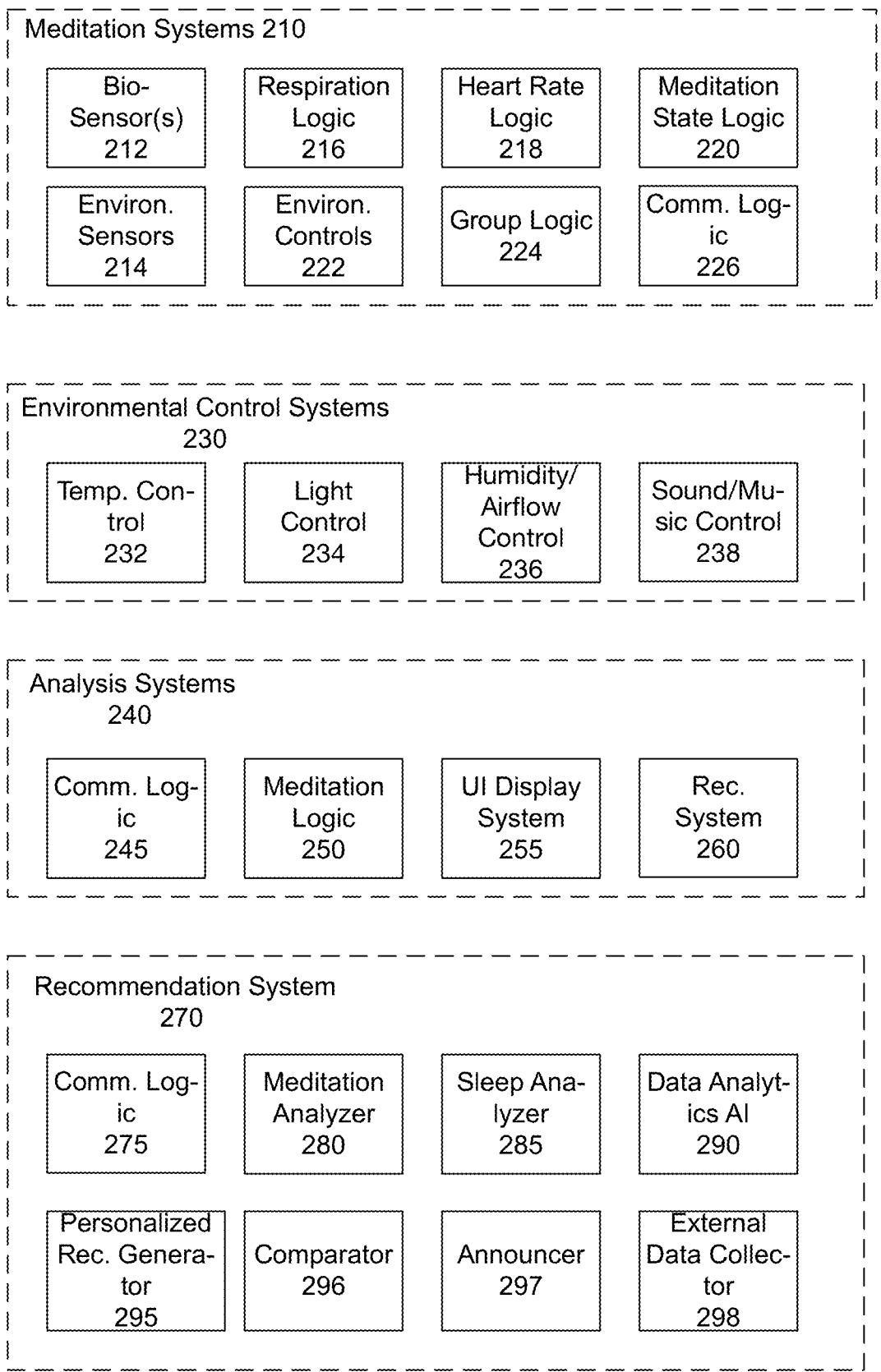
FIG. 2 is a block diagram of one embodiment of the connected meditation system.

FIG. 2 is a block diagram of one embodiment of the connected meditation system. The system in one embodiment includes the meditation system 210, environmental control systems 230, analysis systems 240, and recommendation system 270. Although each of these elements is illustrated separately, these functionalities may be shared by the various devices described with respect to FIG. 1. For example, the meditation system 210 may include the meditation surfaces, a mobile device, and local/environmental controls. Similarly, a single device may provide the functionality of analysis systems 240 and recommendation system 270, or those functionalities may be split among multiple devices.

The meditation systems 210 include a plurality of bio-sensors 212 and environmental sensors 214, in one embodiment. Bio-sensors may include sensitive motion sensors, as well as temperature sensors for the user's body, blood pressure sensors, etc. In one embodiment, bio-sensors 212 are inductive sensors built into the meditation surface. In one embodiment, the sensors 212 are designed to be rolled up (if implemented in a meditation mat), and otherwise handled without damage.

Environmental sensors 214 may include environmental temperature, light level, sound, humidity, and other measurements which may influence the user's ability to meditate.

In one embodiment, meditation system 210 includes a special purpose signal processor to process the data from sensors 212, 214. The processed sensors are used by a special purpose computing system to provide respiration logic and heart rate logic to calculate the respiration and heart rate, and meditation state. In one embodiment, the computing system may be a distributed computing system with a portion of the processing occurring on the meditation system 210 and a portion occurring on a remote processor coupled to the meditation system 210 via communications logic 226.

Respiration logic 216 utilizes data from bio-sensors 212 to calculate the user's respiration (breathing patterns). Such patterns are characteristic of meditation. Various types of meditation generally have different breathing patterns. By calculating the respiration, the system can compare the user's breathing pattern to the breathing pattern of the selected meditation method. Heart rate logic 218 determines the user's heart rate. During meditation, heart rate generally drops.

Meditation state logic 220 utilizes the data from the bio-sensors 212 and the analyzed data from respiration logic 216 and heart rate logic 218. In one embodiment, environmental controls 222 may be utilized to adjust the environmental conditions in the meditation area.

The environmental controls 222 send data to environmental control systems 230. In one embodiment, one or more controls may exist in a system. For example, the control system 222 may turn on a sound/music control 238 to add white noise machine, music, or other sounds. The environmental controls 222 for example may adjust the temperature control 232, to adjust the temperature to improve meditation. The environmental controls 222 for example may adjust the light control 234 to alter the lighting level. Humidity/airflow control 236 may also be adjusted.

The meditation system 210 further includes a communication logic 226. The communication logic 226 enables the meditation system 210 to communicate with other systems, including in one embodiment environmental controls 222. The communication logic 226 may be a wireless connection.

In one embodiment, the meditation system 210 includes a group logic 224. When the meditation is taking place in a group environment, in one embodiment, the meditation surfaces connect to each other. In one embodiment, controls are then provided to one "leader."

Analysis system 240 in one embodiment resides on a server and provides AI analytics. In one embodiment, the analysis system 240 is a server computer system which receives data from the meditation system 210 via communication logic 245. The analysis system 240 in one embodiment, stores this data in a buffer or memory, and utilizes it to provide analytics on the user's meditation session. Furthermore, the analysis system in one embodiment provides the processed data to the recommendation system 270. In one embodiment, meditation logic 250 evaluates the data from a large number of users and provides analytics. In one embodiment, the meditation logic 250 utilizes, in addition to the data from the various meditation sessions, user characteristic data.

User characteristics, in one embodiment include permanent characteristics such as age, gender, permanent health conditions. User characteristics, in one embodiment, further include changeable characteristics such as athletic level, current illnesses or other issues affecting meditation capability or sleep.

Additionally, the meditation logic 250 may user environmental data, such as the user's location, time of day, and environmental characteristics. The meditation logic 250 in one embodiment uses a deep learning system that creates correlations between users and environments. This data is then passed to the recommendation system 260. In one embodiment, the recommendation system 260 creates "ideal" recommendations for users with particular characteristics.

In one embodiment, analysis system 240 further includes a user Interface Display System 255, which calculates and provides to the user statistics about the user's meditation patterns. In one embodiment, the user interface further provides recommendations. FIG. 4B is an exemplary user interface showing the user interface.

The recommendation system 270 receives the data from individual users as well as the analytics data from analysis system 240, via communication logic 275. The recommendation system 270 in one embodiment is a computer system, such as a server or distributed computer system. The data received in one embodiment is stored in a buffer and/or memory.

Meditation analyzer 280 analyzes the user's meditation data and provides feedback. In one embodiment, the determination of the meditation level is done here. In one embodiment, the output of the meditation analyzer 280 is the graph shown in FIG. 4B, showing the dreamy, light, and deep meditation states over the meditation session.

Data analytics AI system 290 utilizes the meditation data and other user data, along with analytics data to build up a set of analytics. In one embodiment, a deep learning system is used.

In one embodiment, the data analytics AI system 290 may also receive data from a sleep analyzer 285. Sleep analyzer 285 receives sleep data from a sleep surface such as a smart bed. Because meditation and sleep are two sides of the same coin—the release of stress and refreshing of the mind. By combining recommendations and analytics in one embodiment, the system can provide recommendations to improve sleep using meditation, to recover from lost sleep using meditation, etc. In one embodiment, the system may also receive data from an activity monitor, such as a mobile device or wrist-worn device which monitors the user's activity level.

Personalized recommendation generator 295 recommends meditation and/or sleep actions for the user. In one embodiment, the personalized recommendation system suggests the timing of subsequent meditation sessions, for optimum impact.

Comparator 296 compares the user's meditation data to the data of comparable users. In one embodiment, the comparable users may be identified by the data analytics AI system 290. In one embodiment, comparable users are users with similar user characteristics (age, gender, athletic ability), and similar behavioral characteristics (sleep patterns, meditation habits, etc.) In one embodiment, comparable users also include users with better habits, and the personalized recommendation generator 295 recommends improvements to the user's behaviors.

External data collector 298 may obtain data from the sleep monitor, activity monitor, and other data sources, to improve the recommendations for the user. In one embodiment, the recommendation generator 295 may also provide other recommendations, such as eating, sleeping, or activity changes.

Figure 3A:
FIGS. 3A-3C are diagrams of exemplary embodiments of physical implementations of the meditation system's sensor surface.
Figure 3B:
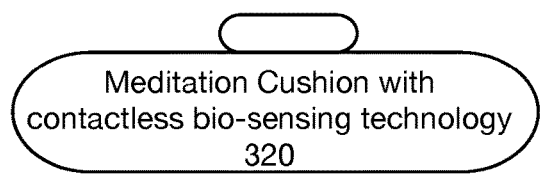
Figure 3C:
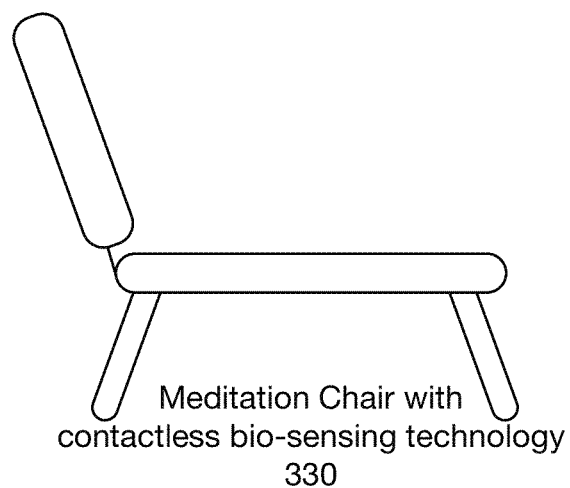
Figure 3C:
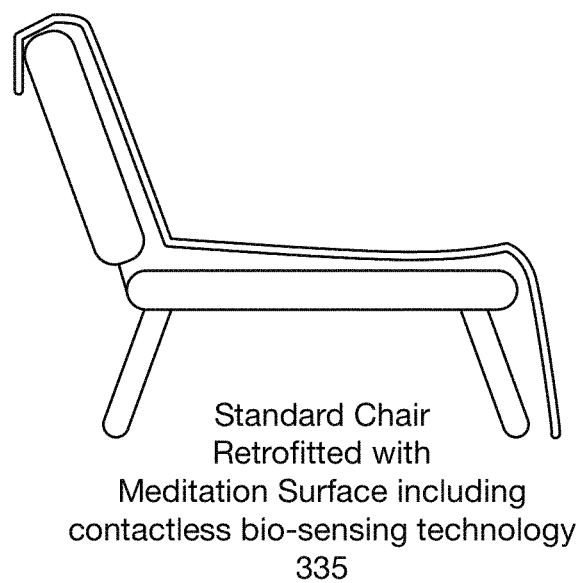

FIGS. 3A-3C are diagrams of exemplary embodiments of physical implementations of the meditation system's sensor surface. The meditation surface may be a meditation mat 310 with contactless bio-sensing technology. In one embodiment, the meditation mat 310 is similar in appearance and use to a standard meditation mat or yoga mat. The sensors are built into the mat, using a flexible semiconductor. In one embodiment, this enables the meditation mat 310 to be rolled as a normal mat would be, without damaging the system.

In one embodiment, the meditation surface is a meditation cushion. Meditation cushions lift the user up from the ground slightly and provide additional cushioning. In one embodiment, the meditation cushion 320 includes a seating area and a small booster cushion for a correct meditation form. For such a cushion, the embedded bio-sensing technology may be positioned in the seating area of the cushion. In one embodiment, the booster may also include sensors.

The meditation surface may also include a meditation chair 330 with contactless bio-sensing technology. The chair may be a special-purpose chair, or an office chair or dining room chair. In one embodiment, the chair may be a standard chair retrofitted with a meditation surface 335. By having a spectrum of meditation surfaces, the system can be used by anyone, regardless of their age, mobility, health, and other constraints. While the above description includes some meditation surfaces, it should be understood that additional meditation surfaces may be utilized, without departing from the scope of the invention.

Figure 3D:
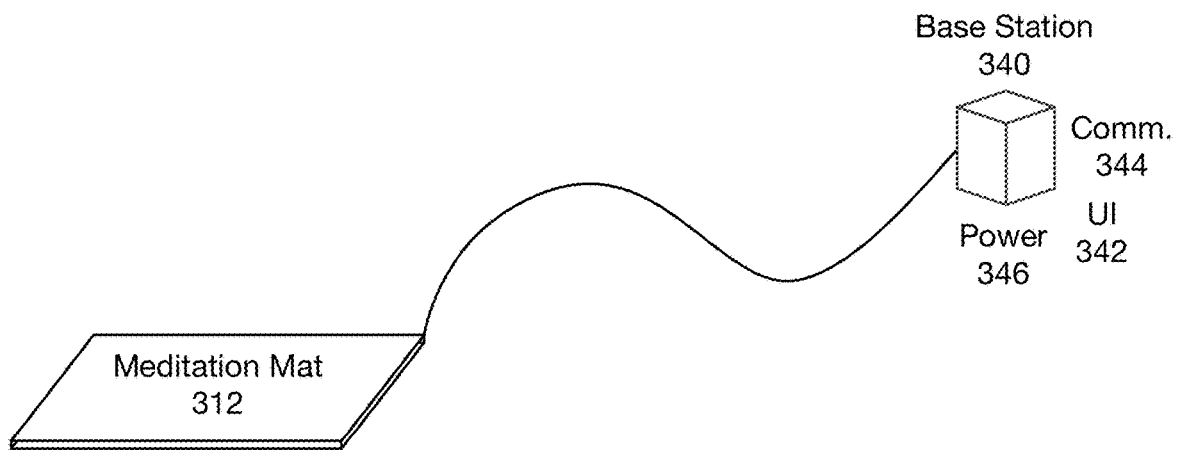
FIGS. 3D-3F are diagrams of different embodiments of providing connectivity to the meditation system.
Figure 3E:
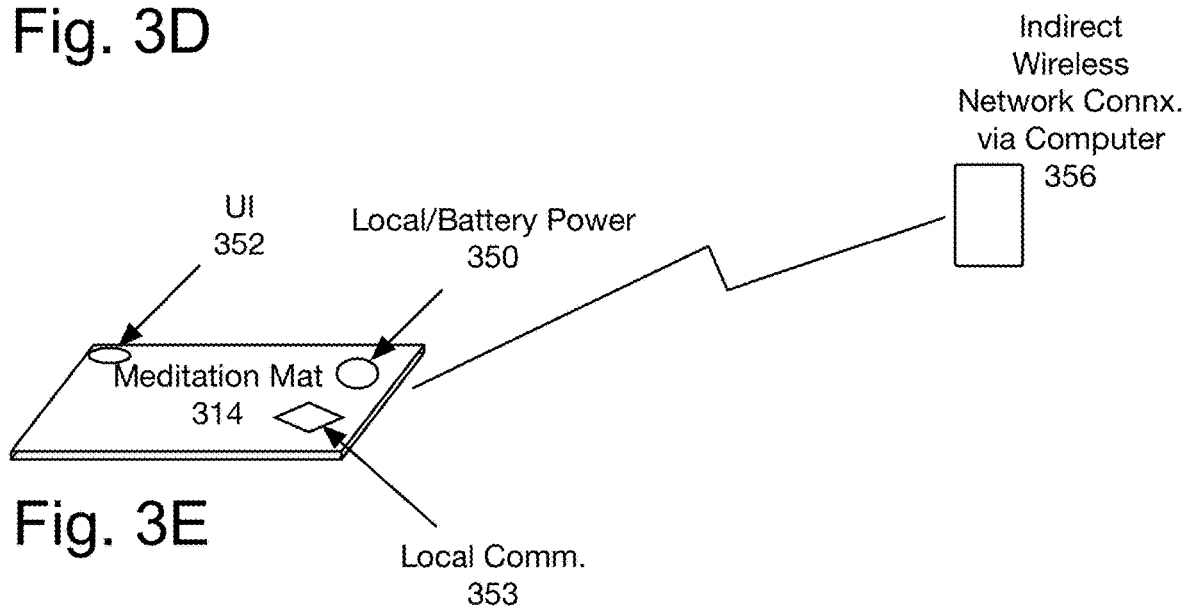

FIGS. 3D-3E are diagrams of different embodiments of providing connectivity to the meditation system. While the examples utilize the meditation mat as the meditation surface, it should be understood that any meditation surface may have any, or all, of these connection approaches.

FIG. 3D illustrates one embodiment of a physically linked connection mat 310. The connection mat 312 is linked to a base station 340. The base station 340 provides power 346 and communication connectivity 344 to the mat 312. In one embodiment, the base station may be coupled via a thin cord. In one embodiment, the base station may be a cube, as illustrated. However, the base station may be a small puck, which can be easily wrapped into a rolled-up meditation mat 312. The base station 340 may provide user interface features, including on one embodiment feedback mechanisms, and displays.

The base station 340 in one embodiment is designed to be plugged into the wall. In another embodiment, the base station 340 may have a batter or other power source. The communication 344 may be provided by a wireless transmitter, a wired Internet connection, a cellular network connection, or other network connector. This interface may be referred to as a meditation surface with a wired network connection.

FIG. 3E illustrates another embodiment of the system in which the meditation mat 314 includes a local power source 350 and local communicator 535. The local power source 350 may be a battery. In one embodiment, the local power source 350 may be a button sized battery. Because the system uses relatively little power, communicating only locally through a low power method in one embodiment, a small button battery may last as long as 3 to 6 months without replacement or recharging. The battery 350 in one embodiment may be a rechargeable battery.

Local communicator 353 in one embodiment connects wirelessly to a computer device, such as the user's mobile device 356. The computer may also be a laptop or desktop equipped with local communication. The local communication connector 353 in one embodiment may be a Bluetooth connection. The mobile device 356 may be a cellular telephone, tablet, or other device. The mobile device 356 may then provide connection to the server through its own communication method. This connectivity can be referred to as meditation surface with indirect wireless network communication.

The computer 356 may provide connectivity as well as a user interface. In one embodiment, the meditation mat 314 includes a user interface 352. The user interface 352 may provide feedback to the user during, or after the meditation session. The user interface 352 may include in one embodiment a light (in one embodiment a multi-colored LED), vibration, sound, or other output mechanism. In one embodiment, the user feedback 352 may be calibrated to not interrupt the user's meditation session. For example, the user interface 352 may be a light which changes colors based on the user's meditation state and indicates the end of a meditation session—if a session length is set.

Figure 3F:
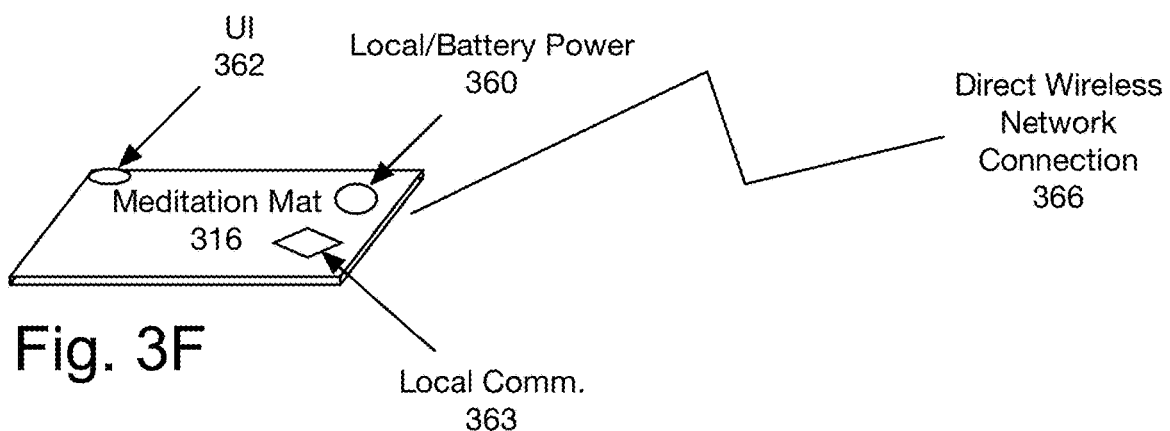

FIG. 3F illustrates another embodiment, in which the meditation mat 316 is self-contained, and includes a local power source 360 and a local communication connection 363. The local communication connection 363 in one embodiment enables the meditation mat 310 to connect to the server via a wireless or cellular network connection. This interface may be referred to as a meditation surface with a direct wireless network connection. The self-contained mat 316 may also include a UI 362.

Figure 3G:
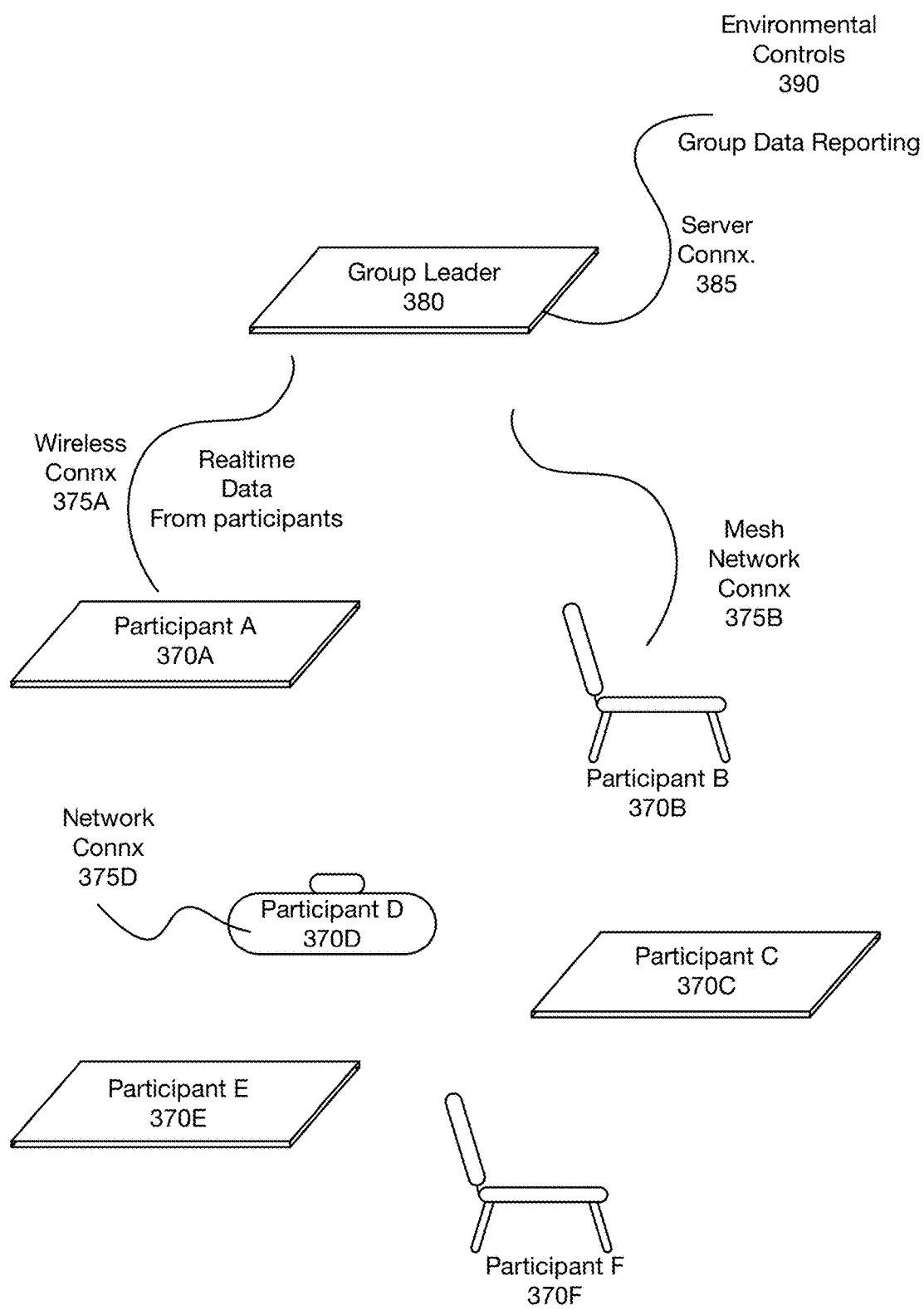
FIG. 3G is a diagram of one embodiment of a group meditation setting.

FIG. 3G is a diagram of one embodiment of a group meditation setting. In this setting, there are a plurality of participants A-F, with a plurality of meditation surfaces which include meditation mats 370A, 370C, 370E, cushions 370D, and chairs 370B, 370F. The group meditation is led by a group leader 380, here illustrated has using a meditation mat. The group leader 380 controls the meditation session.

Figure 4A:
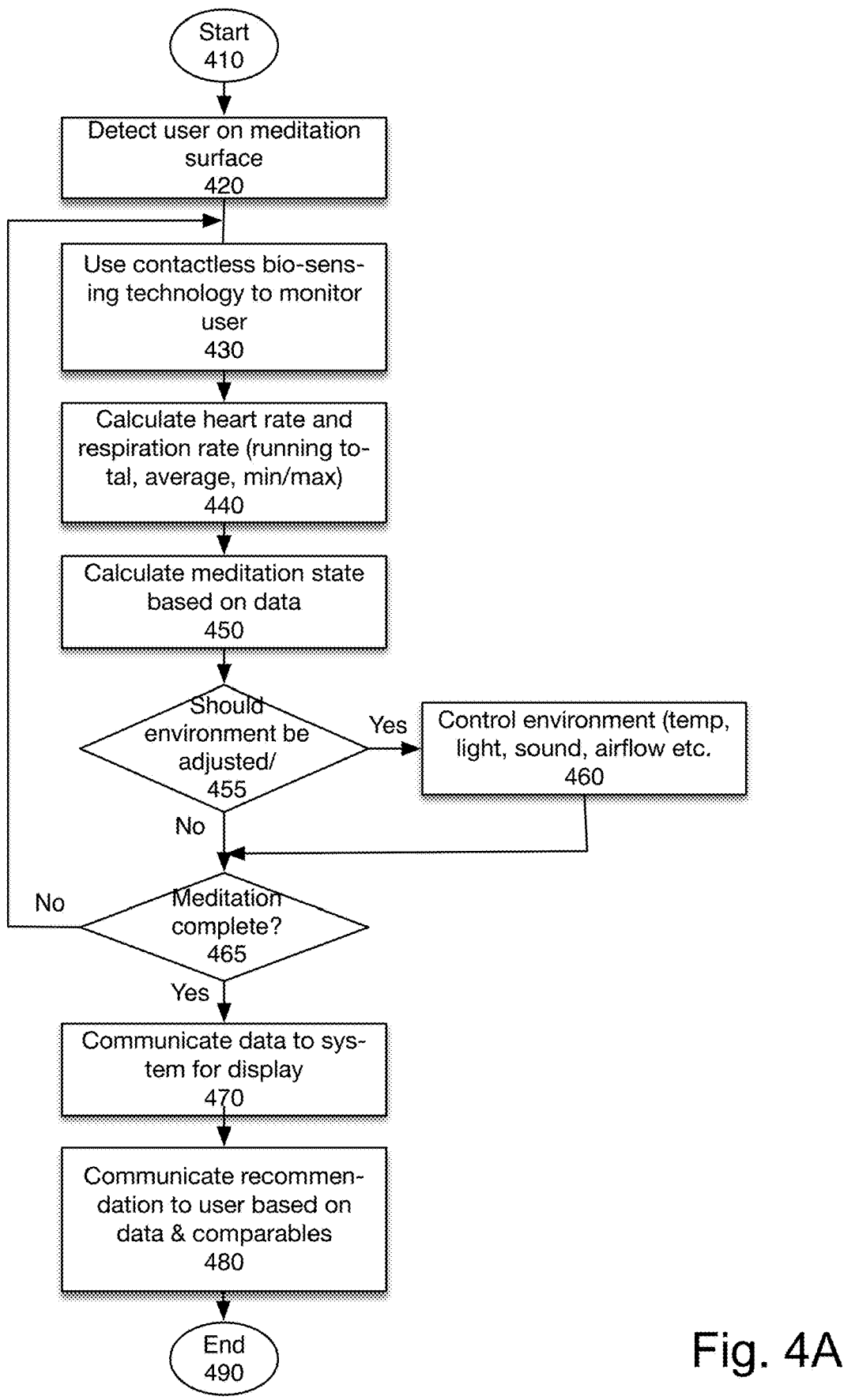
FIG. 4A is a flowchart of one embodiment of using the system.
Figure 4B:
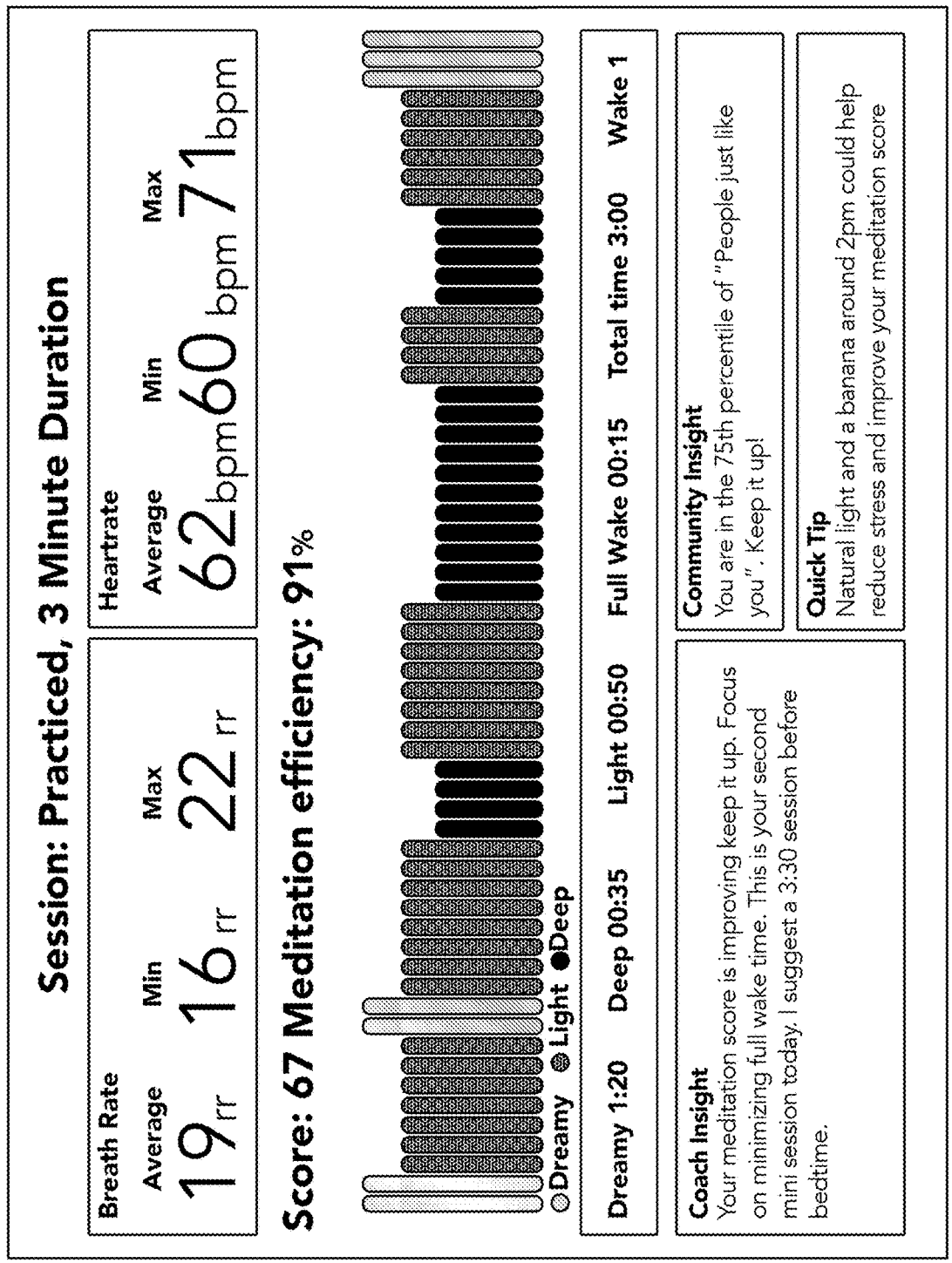
FIG. 4B is an exemplary user interface showing the results of a meditation session.

FIG. 4A is a flowchart of one embodiment of using the system. The process starts at block 410. At block 420, the user is detected on a meditation surface.

At block 430, a contactless biosensing technology is used to monitor the user. The technology may be piezoelectric inertial sensors which measures changes in force but do not measure static/constant forces. The piezoelectric material generates charge in reaction to changes in force and that charge dissipates over time. That makes such piezoelectric inertial sensors particularly well suited for measuring vital signs which involving constantly changing forces (breathing and heart rate). In one embodiment, in addition to an inertial sensor, the system may include a pressure sensor, to measure static pressure. In one embodiment, there is a combination of a pressure sensitive array/mat as well as one or more discrete piezoelectric sensors for the optimal combination of monitoring. In one embodiment, a flexible piezoelectric sensor array is used.

At block 440, the process calculates the user's vital signs, which may include the user's heart rate and respiration rate. In one embodiment the system continuously monitors to provide a running average, as well as minimum/maximum values for these vital signs.

At block 450, the process calculates the meditation state of the user based on the data. Meditation generally lowers heart rate and respiration, and different types of meditation have different breathing patterns.

At block 455, the process determines whether the user's environment should be adjusted. For example, if it is excessively cold, meditative states may be harder to achieve. Similarly, if it is very bright, deeper meditation may be harder. If the system determines that an environmental adjustment should be made, at block 460 the environment is adjusted. In one embodiment, this is done by interfacing with smart home elements which may allow the system to adjust light levels, sound levels, air flow, and/or other environmental factors.

At block 465, the process determines whether the meditation session is complete. In one embodiment, completion is determined when the user leaves the meditation surface.

At block 470, the process communicates data to the system for display. The display may provide data about the user's meditation length, breath rate, heart rate, etc. In one embodiment, the display also provides data about the user's meditation efficiency.

At block 480, the system communicates a recommendation to the user, based on the data and data from prior meditation sessions of the user, data from meditation sessions by other users who are comparable, or data from other sources. FIG. 4B illustrates one embodiment of the data that is made available to the user. In one embodiment, the user's data is communicated anonymously to a server which provides recommendations based on machine learning and the analysis of large volumes of data. The process then ends at block 490.

Figure 5:
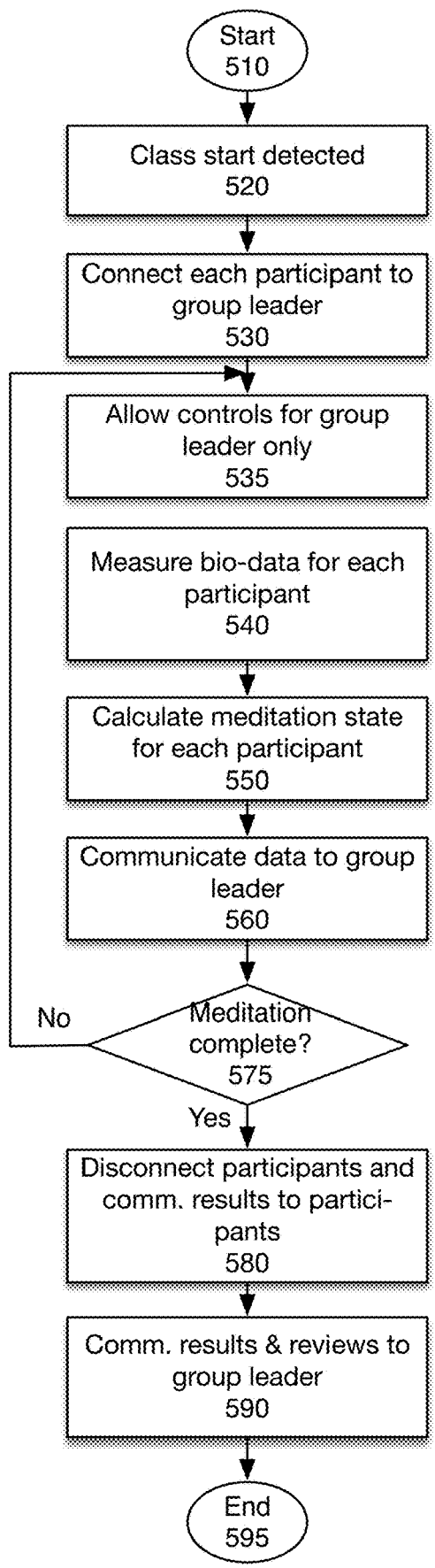
FIG. 5 is a flowchart of one embodiment of using the system in a group meditation setting.

FIG. 5 is a flowchart of one embodiment of using the system in a group meditation setting. The process starts at block 510. At block 520, a class start is detected. At block 530, each participant is connected to the group leader. In one embodiment, each meditation surface associated with someone other than the leader is in "follower" mode, while the meditation surface of the leader retains controls, at block 535.

At block 540, the bio-data of each user is measured. At block 550, the meditation state for each participant is calculated.

At block 560, the data is communicated to the meditation group leader. In one embodiment, the data is communicated through a simple user interface which shows the meditation state of each user in the group. In one embodiment, the meditation state may be shown by color. For example, the color may be red for not in a meditative state, blue for light, and green for deep state. In one embodiment, this enables the group leader to focus on users having difficulty meditating. Additionally, it may allow the group leader to adjust the environment to help those who are having difficulty.

At block 575, the process determines whether the meditation is complete. If not, the process returns to block 540, to provide controls for the group leader an continue monitoring the users. If the meditation is complete, the process continues to block 580.

At block 580, the participants are disconnected, and their meditation results are communicated to them. In one embodiment, the results include comparative results. In one embodiment, the process also allows the user to rate the group sessions. In one embodiment, a combination of the user's meditation state and feedback may be used to recommend, or advise against, future meditation sessions with particular group leaders or orientations.

At block 590, the results and reviews are communicated to the group leader. In one embodiment, if the meditation session was in a class or similar environment, the results may also be communicated to supervisors or others. In one embodiment, the users' data is stripped of identifying information before being used in the machine learning system. In one embodiment, the system may rate the group session and the group leader. The process then ends at block 595.

Figure 6:
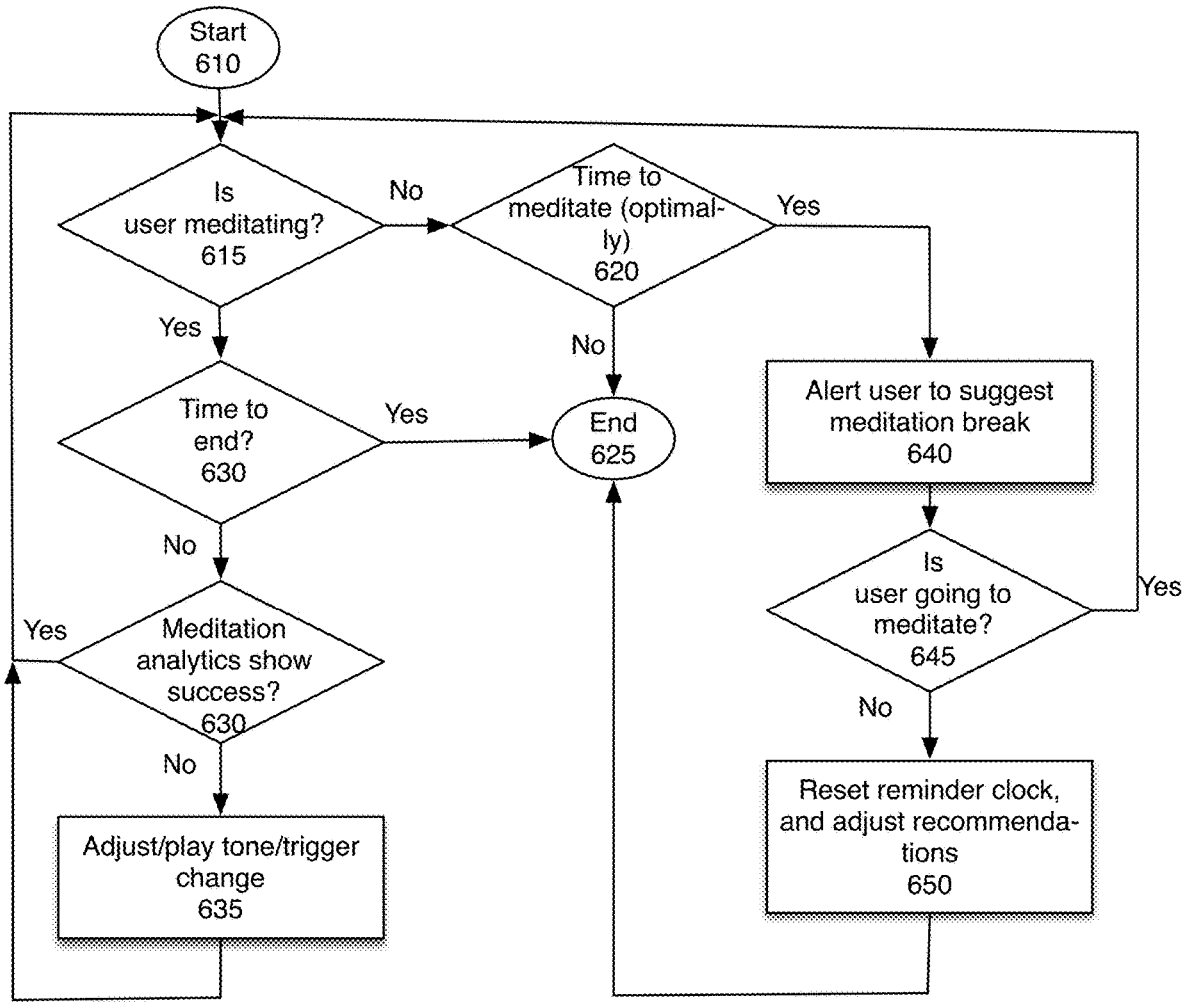
FIG. 6 is a flowchart of one embodiment of improving meditation practice.

FIG. 6 is a flowchart of one embodiment of improving meditation practice. The process starts at block 610.

At block 615, the process determines whether the user is meditating. If not, the process determines whether it is time to meditate. If not, the process ends at block 625. If it is time to meditate, the process continues to block 640.

At block 640, the user is alerted to suggest taking a meditation break. In one embodiment, the user may set a preferred timing for meditation breaks. For example, the user may set a meditation break in the morning and the afternoon. In one embodiment, the system by default sets two meditation breaks during the school day, and one additional meditation break in the evening.

At block 645, the system determines whether the user is going to meditate. In one embodiment, this is based on the user's response to the alert. If the user indicates that he or she is not going to meditate, the reminder clock is reset. In one embodiment, the user may be reminded once an hour of a missed meditation break. In one embodiment, based on multiple responses, the recommendation/timing may be adjusted for the user. For example, if the user consistently indicates that they will not take a meditation break after an alert at 10 am, but consistently takes a meditation break at 11:30, the timing of the recommendation may be shifted to fit the user's real schedule. The process then ends, at block 625.

If the user indicates that he or she is going to meditate, the process returns to block 615 to determine whether the user is meditating.

If, at block 615, the process determined that the user is meditating, the process continues to block 630. At block 630, the process determines whether it's time to end the meditation session. In one embodiment, an meditation session may be timed based on elapsed time (e.g. 15 minutes), or on time spent in a deep meditation state (e.g. 5 minutes), or on the user's body (e.g. when the user comes out of deep meditation after a minimum time is elapsed). In one embodiment, the user is alerted when it's time to end the session. The process then ends at block 625.

If it is not yet time to end the meditation session, at block 630, the process determines whether the meditation analytics show that the user has successfully entered a deep meditative state. If the user has successfully entered a meditative state, the process continues to block 615 to continue monitoring the user.

Otherwise, at block 635, the process attempts to make a change to assist the user into the meditative state. In one embodiment, the change may include a change to the user's environment (for example lowering the lights, adjusting the temperature, utilizing a tone or scent to assist). In one embodiment, the process notes which of the attempted adjustments are successful and associates those adjustments with this user. In one embodiment, that data is also provided to the deep learning system. The process then continues to block 615, to continue monitoring the user.

Figure 7:
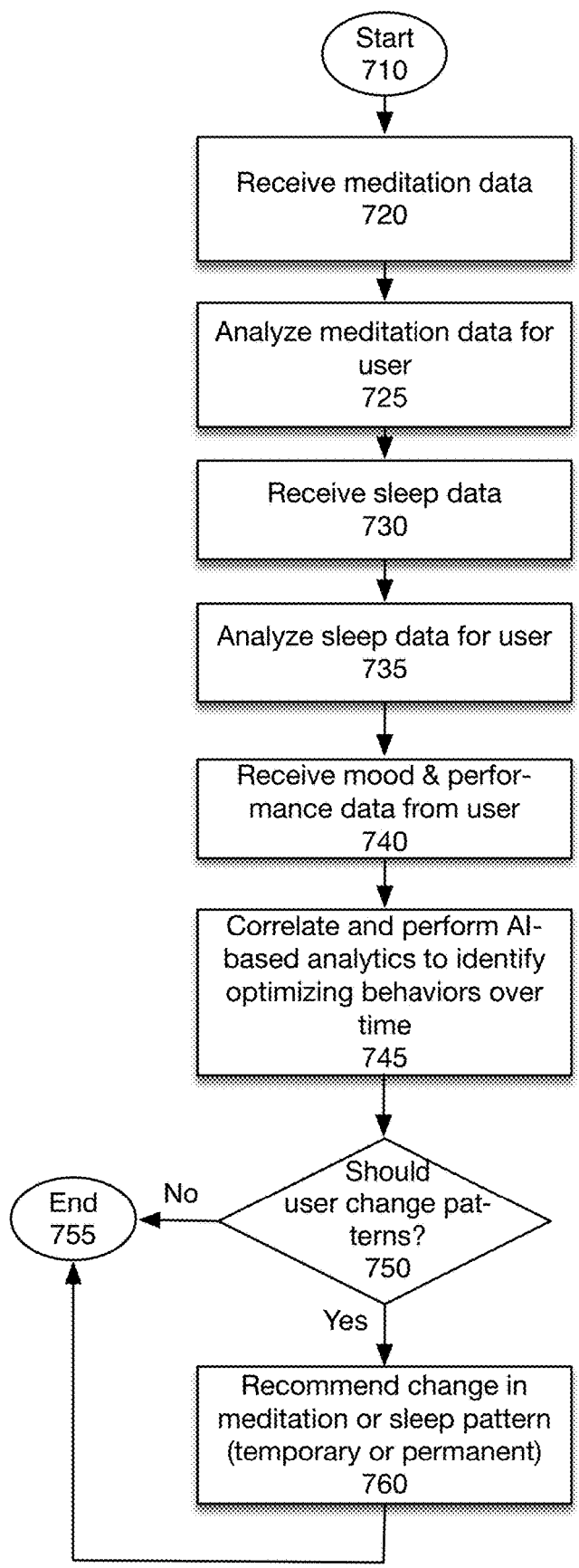
FIG. 7 is a flowchart of one embodiment of using correlation to align the user's behavior based on information from the meditation system.

FIG. 7 is a flowchart of one embodiment of using correlation to align the user's behavior based on information from the meditation system. The process starts at block 710. At block 720, the server/process receives the meditation data. The data is analyzed, at block 725. At block 730, the user's sleep data is received if available. At block 735, the sleep data is analyzed. At block 740, the system receives mood and performance data from the user. In one embodiment, this is provided by the user on a regular basis. For example, the user may be asked by the system periodically how they feel, and how they are performing. In one embodiment, performance data may also be received from a system which monitors the user's activity, e.g. running speed and endurance may be received from a health monitoring system.

At block 745, the data is correlated and AI-based analytics are used to identify optimizing behaviors over time. In one embodiment, the correlation determines the interaction between the timing and depth of the meditation, the timing and depth of the user's sleep, and the user's mood and performance. In general, it is expected that regular meditation improves mood and sports performance, as well as work performance and focus.

At block 750 the process determines whether the user should change his or her patterns. In one embodiment, this determination is made based on continuous data over time. If there is no need to change patterns, at block 755 the process ends. Otherwise, the system recommends a change in the meditation or sleep pattern. In one embodiment the recommendation may be for a temporary change to see if making a change would make a difference in the user's mood or performance. The process then ends.

Of course, though FIGS. 4A, 5, 6, and 7 are shown as flowcharts, in one embodiment the ordering of the steps may be varied, unless the steps are directly dependent on each other. Furthermore, various decisions may be implemented as an interrupt-driven elements, rather than processing through a flow to reach those points.

Figure 8:
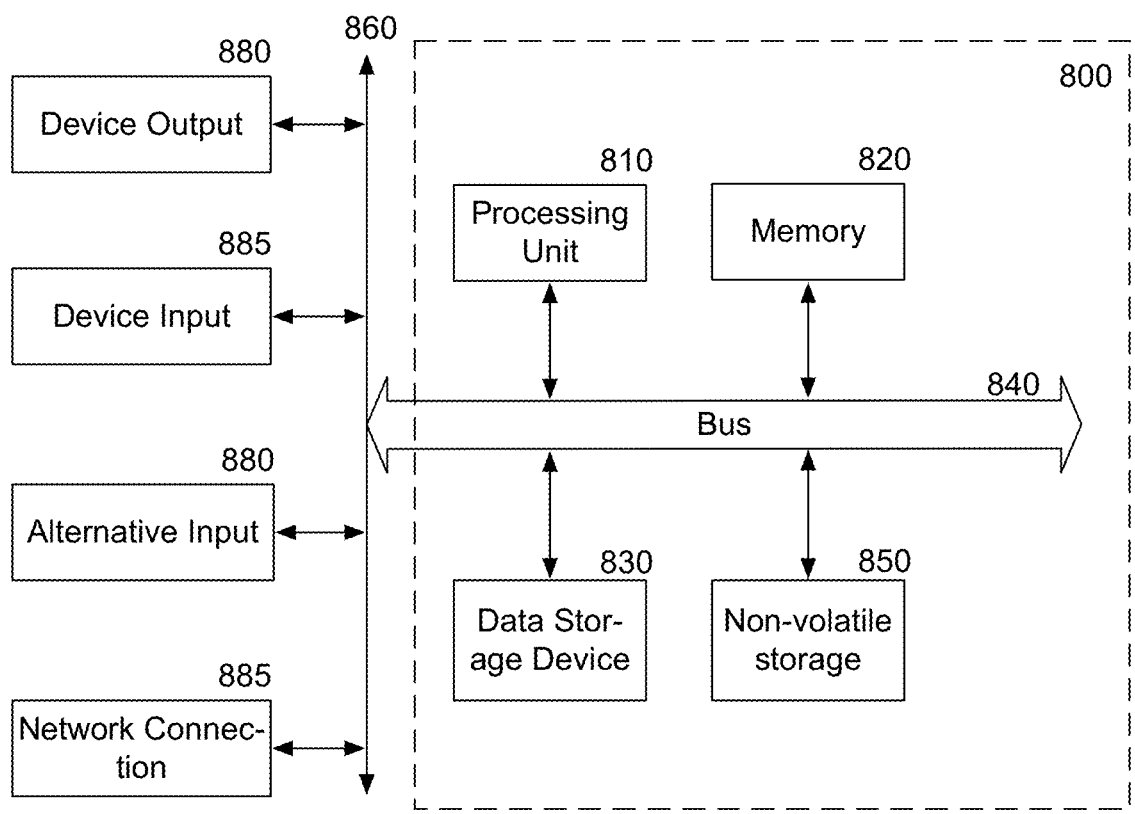
FIG. 8 is a block diagram of one embodiment of a computer system that may be used with the present invention.

FIG. 8 is a block diagram of one embodiment of a computer system that may be used with the present invention. It will be apparent to those of ordinary skill in the art, however that other alternative systems of various system architectures may also be used.

The data processing system illustrated in FIG. 8 includes a bus or other internal communication means 840 for communicating information, and a processing unit 810 coupled to the bus 840 for processing information. The processing unit 810 may be a central processing unit (CPU), a digital signal processor (DSP), or another type of processing unit 810.

The system further includes, in one embodiment, a random access memory (RAM) or other volatile storage device 820 (referred to as memory), coupled to bus 840 for storing information and instructions to be executed by processor 810. Main memory 820 may also be used for storing temporary variables or other intermediate information during execution of instructions by processing unit 810.

The system also comprises in one embodiment a read only memory (ROM) 850 and/or static storage device 850 coupled to bus 840 for storing static information and instructions for processor 810. In one embodiment, the system also includes a data storage device 830 such as a magnetic disk or optical disk and its corresponding disk drive, or Flash memory or other storage which is capable of storing data when no power is supplied to the system. Data storage device 830 in one embodiment is coupled to bus 840 for storing information and instructions.

The system may further be coupled to an output device 870, such as a cathode ray tube (CRT) or a liquid crystal display (LCD) coupled to bus 840 through bus 860 for outputting information. The output device 870 may be a visual output device, an audio output device, and/or tactile output device (e.g. vibrations, etc.)

An input device 875 may be coupled to the bus 860. The input device 875 may be an alphanumeric input device, such as a keyboard including alphanumeric and other keys, for enabling a user to communicate information and command selections to processing unit 810. An additional user input device 880 may further be included. One such user input device 880 is cursor control device 880, such as a mouse, a trackball, stylus, cursor direction keys, or touch screen, may be coupled to bus 840 through bus 860 for communicating direction information and command selections to processing unit 810, and for controlling movement on display device 870.

Another device, which may optionally be coupled to computer system 800, is a network device 885 for accessing other nodes of a distributed system via a network. The communication device 885 may include any of a number of commercially available networking peripheral devices such as those used for coupling to an Ethernet, token ring, Internet, or wide area network, personal area network, wireless network or other method of accessing other devices. The communication device 885 may further be a null-modem connection, or any other mechanism that provides connectivity between the computer system 800 and the outside world.

Note that any or all of the components of this system illustrated in FIG. 8 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 820, mass storage device 830, or other storage medium locally or remotely accessible to processor 810.

It will be apparent to those of ordinary skill in the art that the system, method, and process described herein can be implemented as software stored in main memory 820 or read only memory 850 and executed by processor 810. This control logic or software may also be resident on an article of manufacture comprising a computer readable medium having computer readable program code embodied therein and being readable by the mass storage device 830 and for causing the processor 810 to operate in accordance with the methods and teachings herein.

The present invention may also be embodied in a handheld or portable device containing a subset of the computer hardware components described above. For example, the handheld device may be configured to contain only the bus 840, the processor 810, and memory 850 and/or 820.

The handheld device may be configured to include a set of buttons or input signaling components with which a user may select from a set of available options. These could be considered input device #1 875 or input device #2 880. The handheld device may also be configured to include an output device 870 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose computing system including a subset of the computer hardware components described above. For example, the special purpose computing system may include a processing unit 810, a data storage device 830, a bus 840, and memory 820, and no input/output mechanisms, or only rudimentary communications mechanisms, such as an LED based feedback system. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 885.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 810. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized, and that logical, mechanical, electrical, functional and other changes may be made without departing from the scope of the present invention. The following detailed description is, therefore, not to be taken in a limiting sense, and the scope of the present invention is defined only by the appended claims.

We claim:

1. A meditation system comprising:
   a meditation surface, capable of supporting a meditating user, including a contactless bio-sensor, the contactless bio-sensor being internal to the meditation surface;
   a processor to analyze data from the contactless bio-sensor, the data collected and analyzed during a time when the user is meditating, the processor's analysis to determine meditation results of the meditating user including the user's respiration, heart rate, and meditation quality while the user is meditating;
   the processor to calculate a recommendation for the user to improve the user's meditation, based on the meditation results; and
   a user interface to display the meditation results and the recommendation, while the user is meditating.

2. The meditation system of claim 1, further comprising:
   a user interface to provide real-time data to the user about the meditation quality.

3. The meditation system of claim 1, further comprising:
   environmental controls to adjust Internet-of-Things (IoT) controlled environmental elements, to improve the user's meditation quality.

4. The meditation system of claim 1, further comprising:
   a group logic to enable a teacher to guide the user of the meditation system in group meditation.

5. The meditation system of claim 4, wherein student meditation systems are subordinated to a teacher meditation system, during the group meditation.

6. The meditation system of claim 1, further comprising:
   a recommendation system to recommend a meditation practice to the user, based on the meditation results.

7. The meditation system of claim 6, wherein the meditation practice includes timing of meditation sessions.

8. A method of enhancing a meditation session comprising:
   monitoring a user's biometric data using a meditation surface capable of supporting the meditating user including a contactless bio-sensor during a time when a user is meditating, where the contactless bio-sensor is internal to the meditation surface;
   analyzing data from the contactless bio-sensor when the user is meditating, the processor's analysis to determine meditation results of the meditating user including the user's respiration, heart rate, and meditation while the user is meditating;
   calculating a recommendation to the user to improve the user's meditation, based on the meditation results; and
   displaying the meditation results and the recommendation, while the user is meditating.

9. The method of claim 8, further comprising:
   providing real-time data to the user about the meditation quality.

10. The method of claim 8, further comprising:
    enabling automatic adjustment of environmental elements using an Internet-of-Things (IoT) interface, to improve the user's meditation quality.

11. The method of claim 8, further comprising:
    guiding the user in a group meditation, using a single teacher guiding a group of one or more users.

12. The method of claim 11, wherein student meditation systems are subordinated to a teacher meditation system, during the group meditation.

13. The method of claim 8, further comprising:
recommending a meditation practice to the user, based on the meditation results.

14. The method of claim 13, wherein the meditation practice includes timing of meditation sessions.

15. A meditation system comprising:
a group leader meditation system, including a first meditation surface including a first contactless bio-sensor;
one or more participant meditation systems usable by a plurality of meditating users, each participant meditation system including:
a meditation surface and a contactless bio-sensor internal to the meditation surface, the meditation surface capable of supporting a respective one of the meditating users;
a processor configured to analyze data from the contactless bio-sensor, to determine the respective user's meditation state, while the respective user is meditating;
a connection to the group leader meditation system;
a group leader processor configured to receive the meditation state from the one or more participant meditation systems while the plurality of meditating users are meditating; and
each of the one or more participant meditation systems including a user interface configured to display meditation results at an end of a meditation session, the meditation results including data from the group leader meditation system.

16. The meditation system of claim 15, further comprising:
a user interface to show the meditation state of each user.

17. The meditation system of claim 15, further comprising:
environmental controls configured to enable adjustment of a meditation environment by a group leader, based on the meditation results from the one or more participant meditation systems.

18. The meditation system of claim 15, further comprising:
a recommendation system configured to recommend a meditation practice to the user, based the meditation results from a plurality of meditation sessions.

19. The meditation system of claim 1, wherein the meditation quality determined by the processor further includes a determined meditative state of the user, the meditative state comprising at least one of: a light meditative state, a dreamy meditative state, and a deep meditative state.

20. The meditation system of claim 1, wherein the contactless bio-sensor comprises a contactless piezoelectric inertial sensor internal to the meditation surface, which measures changes in force, while the user is meditating, but does not measure static/constant forces.

21. The meditation system of claim 1, where the recommendation is displayed while the user is meditating.

22. The meditation system of claim 1, where the user interface is integral to the meditation surface.

* * * * *